United States Patent [19]

Bernareggi et al.

[11] Patent Number: 4,558,054

[45] Date of Patent: Dec. 10, 1985

[54] SPASMOLYTIC ENDO-8,8-DIALKYL-8-AZONIABICYCLO (3.2.1) OCTANE-6,7-EXO-EPOXY-3-ALKYL-CARBOXYLATE SALTS

[75] Inventors: Virgilio Bernareggi; Fausto Bonifacio; Roberto Margutti; Maurizio Fano, all of Milan, Italy

[73] Assignee: Valeas S.p.A., Milan, Italy

[21] Appl. No.: 628,398

[22] Filed: Jul. 6, 1984

[30] Foreign Application Priority Data

Jul. 26, 1983 [IT] Italy ............... 22238 A/83

[51] Int. Cl.4 ............... C07D 491/10; A61K 31/655
[52] U.S. Cl. ............... 514/291; 546/91
[58] Field of Search ............... 546/91; 424/256, 265; 514/291

[56] References Cited

U.S. PATENT DOCUMENTS 3,472,861  10/1969  Zeile et al. ............... 546/91

Primary Examiner—Henry R. Jiles
Assistant Examiner—Dale A. Bjorkman
Attorney, Agent, or Firm—Stevens, Davis, Miller & Mosher

[57] ABSTRACT

The invention relates to new products, namely endo-8,8-dialkyl-8-azoniabicyclo [3.2.1] octane-6,7-exo-epoxy-3-alkylcarboxylates, of formula:

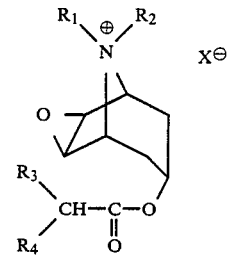

in which $R_1$ and $R_2$, which can be the same or different, are linear or branched alkyl radicals of 1–5 C atoms or cycloalkyl radicals of 3–6 C atoms;

$R_3$ and $R_4$, which can be the same or different, are alkyl radicals of 1–6 C atoms;

$X^-$ is a halide ion.

The new compounds are powerful spasmolytics.

4 Claims, No Drawings

SPASMOLYTIC ENDO-8,8-DIALKYL-8-AZONIABICYCLO (3.2.1) OCTANE-6,7-EXO-EPOXY-3-ALKYL-CARBOXYLATE SALTS

This invention relates to a new class of endo-8,8-dialkyl-8-azoniabicyclo[3.2.1]octane-6,7-exo-epoxy-3-alkylcarboxylates of formula:

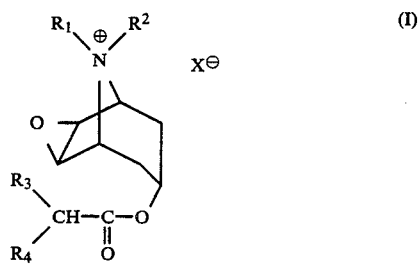

in which $R_1$ and $R_2$, which can be the same or different, are linear or branched alkyl radicals of 1–5C atoms, or cycloalkyl radicals of 3–6C atoms;

$R_3$ and $R_4$, which can be the same or different, are alkyl radicals of 1–6C atoms;

$X^-$ is a halide ion.

The new products demonstrate potent spasmolytic action, unaccompanied by side effects.

The compounds of formula (I) are prepared starting from endo-8-methyl-8-azabicyclo[3.2.1]octane-6,7-exo-epoxy-3-alkylcarboxylates of formula:

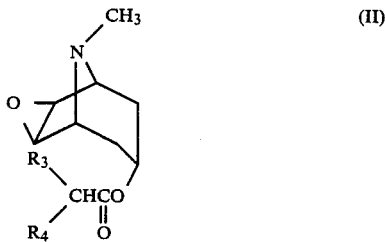

The starting substances (II) are easily obtained by condensing a suitable acyl chloride with scopine, a commercially available product, in accordance with the following equation:

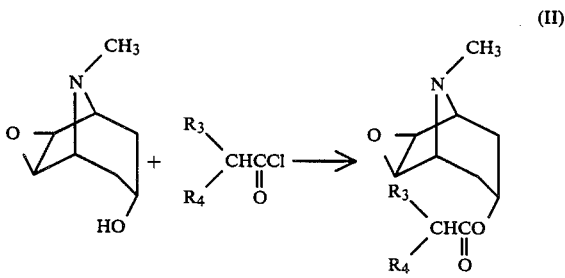

in which $R_3$ and $R_4$ are as heretofore defined.

The compounds of formula (I) can be prepared from the compounds of formula (II) by quaternisation in accordance with two alternatives which lead respectively to the endo-8-methyl-8-anti-alkyl-8-azoniabicyclo derivatives and to the endo-8-alkyl-8-syn-alkyl-8-azoniabicyclo derivatives, by utilising the Fodor rule.

The two alternatives of the process according to the present invention are schematically as follows:

(A) Treating the endo-8-methyl-8-azabicyclo[3.2.1]octane-6,7-exo-epoxy-3-alkylcarboxylates of formula (II) with the suitable alkyl halides to give the corresponding endo-8-methyl-8-anti-alkyl compounds in accordance with the Fodor rule (Fodor et al., Acta Chim. Acad. Sci. Hung. 5, 379-1955)

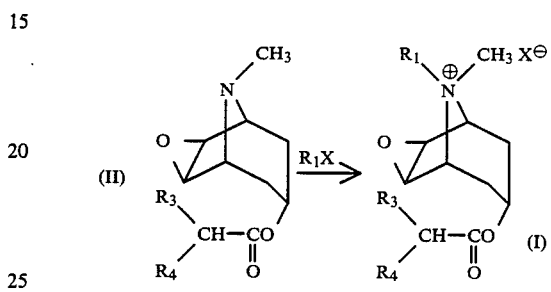

in which $R_1$, $R_3$, $R_4$ are as heretofore defined.

The said quaternisation reaction is preferably conducted by treating the compounds of formula (II) with a large excess of alkyl halide in a suitable organic solvent such as acetone, nitrile, chloroform or methylene chloride, at ambient temperature or in a reaction bomb at high temperature, under an inert atmosphere and obscured from light.

(B) Treating the endo-8-methyl-8-azabicyclo[3.2.1]octane-6,7-exo-epoxy-3-alkylcarboxylates of formula (II) with demethylating agents, alkylating the compound obtained in this manner with alkyl halides to give the corresponding endo-8-alkyl-8-azabicyclo[3.2.1]octane-6,7-exo-epoxy-3-alkylcarboxylates, quaternising the compounds obtained in this manner with a suitable alkyl halide to give endo-8,8-dialkyl-8-azionabicyclo[3.2.1]octane-6,7-exo-epoxy-3-alkylcarboxylates in accordance with the Fodor rule.

The operational stages of procedure B are represented by the following reaction schemes:

b₁—Demethylation

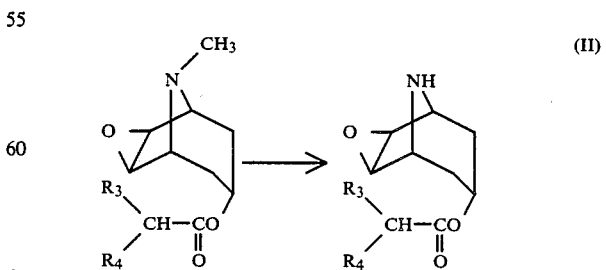

in which $R_3$, $R_4$ are as heretofore defined.

b₂—Alkylation

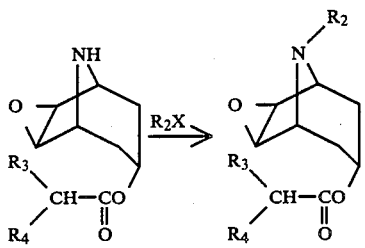

in which $R_2$, $R_3$, $R_4$ are as heretofore defined.

$b_3$—Quaternisation in accordance with Fodor

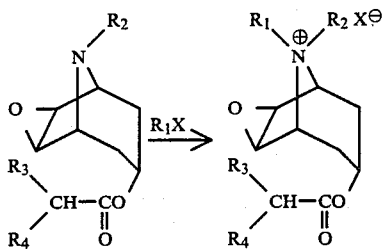

in which $R_1$, $R_2$, $R_3$, $R_4$ are as heretofore defined.

Stage $b_1$ can be effected with demethylating agents such as phosgene or 2,2,2-trichloro-ethyl-chloroformate.

It is preferably effected with phosgene in an organic solvent such as toluene, at a temperature of between $-50°$ and $0°$ C.

Stage $b_2$ is effected by reacting the endo-8-azabicyclo[3.2.1]octane-6,7-exo-epoxy-3-alkylcarboxylate with alkylating agents of formula $R_2X$, in which X is halogen, preferably in the presence of an organic or inorganic acidity acceptor and an inert organic solvent such as acetonitrile at a temperature of between 50° and 100° C.

The quaternisation stage $b_3$ can be effected under the same conditions as those described under point (A).

Some examples of preparation of the new compounds are given hereinafter in order to illustrate some preferred embodiments of the process according to the present invention.

These examples represent non-limiting illustrations of the invention. On the basis of the given description, all possible modifications will be immediately apparent to experts of the art, and these also fall within the scope of the invention.

EXAMPLE 1

Process for preparing endo-8,8-dimethyl-8-azoniabicyclo[3.2.1]octane-6,7-exo-epoxy-3-(2-propyl)-pentoanoate bromide (Compound No. 2 of Table 1—Method A)

Endo-8-methyl-8-azabicyclo[3.2.1]octane-6,7-exo-epoxy-3-(2-propyl)pentanoate.

10.2 g of scopine (0.066 moles) are heated in an anhydrous environment to 80° C., and then 40 ml of dipropylacetylchloride are added under agitation.

The mixture is heated to 80° C. for 8 hours and then dissolved in water, washed with ethyl ether, made basic with $K_2CO_3$ and extracted with chloroform.

The organic phase is evaporated to give an oily crude product which is purified by chromatography over silica using an acetone eluent, to give the required product.

9.6 g of endo-8-methyl-8-azabicyclo[3.2.1]octane-6,7-exo-epoxy-3-(2-propyl)pentanoate are obtained.

Yield: 52%; Acidimetric titre: 99%.

Analysis for $C_{16}H_{27}NO_3 \cdot HCl$:

|  | C | H | N |
| --- | --- | --- | --- |
| Calculated % | 60.44 | 8.88 | 4.41 |
| Found % | 60.81 | 8.92 | 4.30 |

Endo-8,8-dimethyl-8-azoniabicyclo[3.2.1]octane-6,7-exo-epoxy-3-(2-propyl)pentanoate bromide.

2 g of endo-8-methyl-8-azabicyclo[3.2.1]octane-6,7-exo-epoxy-3-(2-propyl)pentanoate (0.007 moles) dissolved in 15 ml of methylene chloride are reacted at ambient temperature with 7 g of $CH_3Br$ for 5 days.

At the end of this period, it is diluted with anhydrous ethyl ether and the precipitate is filtered off to give the required product.

1.5 g of endo-8,8-dimethyl-8-azoniabicyclo[3.2.1]octane-6,7-exo-epoxy-3-(2-propyl)pentanoate bromide are obtained.

Yield: 56%; Melting point: 175°–176° C.

Analysis for $C_{17}H_{30}BrNO_3$:

|  | C | H | N |
| --- | --- | --- | --- |
| Calculated % | 54.25 | 8.03 | 3.72 |
| Found % | 52.61 | 8.06 | 3.40 |

EXAMPLE 2

Process for preparing endo-8-methyl-8-anti-ethyl-8-azionabicyclo[3.2.1]octane-6,7-exo-epoxy-3-(2-propyl)-pentanoate bromide (Compound No. 12 of Table 1—Method A).

Endo-8-methyl-8-anti-ethyl-8-azionabicyclo[3.2.1]octane-6,7-exo-epoxy-3-(2-propyl)pentanoate bromide.

5 g of endo-8-methyl-8-azabicyclo[3.2.1]octane-6,7-exo-epoxy-3-(2-propyl)pentanoate (0.018 moles), prepared in accordance with the procedure described in Example 1, are dissolved in 20 ml of anhydrous acetonitrile and reacted with 13.5 ml of ethyl bromide for 5 hours under reflux.

At the end of this period it is diluted with ethyl ether, the oil which forms is allowed to crystallise, and is filtered off to obtain the required product.

5.9 g of endo-8-methyl-8-anti-ethyl-8-azoniabicyclo[3.2.1]octane-6,7-exo-epoxy-3-(2-propyl)pentanoate bromide are obtained.

Yield: 85%; Melting point: 152°–154° C.

Analysis for $C_{18}H_{32}BrNO_3$:

|  | C | H | N |
| --- | --- | --- | --- |
| Calculated % | 55.38 | 8.26 | 3.59 |
| Found % | 53.93 | 8.29 | 3.40 |

EXAMPLE 3

Process for preparing endo-8-methyl-8-syn-ethyl-8-azionabicyclo[3.2.1]octane-6,7-exo-epoxy-3-(2-propyl)-pentanoate bromide (Compound No. 5 of Table 1—Method B).

Endo-8-azabicyclo[3.2.1]octane-6,7-exo-epoxy-3-(2-propyl)pentanoate.

22 g of endo-8-methyl-8-azabicyclo[3.2.1]octane-6,7-exo-epoxy-3-(2-propyl)pentanoate (0.078 moles), prepared in accordance with the procedure described in Example 1, are dissolved in 50 ml of anhydrous methylene chloride, and 120 ml of 20% phosgene in toluene are added under agitation at 0° C.

After 5 days at ambient temperature the solvent is distilled off under vacuum, the residue taken up in anhydrous ether and the unreacted hydrochloride of the starting substance removed by filtration.

The solvent is removed under vacuum and the residue taken up in 600 ml of 1.5N hydrochloric acid and heated to 70° C. for 1.5 hours.

The clear solution is cooled, washed with ethyl ether, made basic and extracted with methylene chloride.

The solvent is then dried and evaporated to give the required product.

13 g of endo-8-azabicyclo[3.2.1]octane-6,7-exo-epoxy-3-(2-propyl)pentanoate are obtained.

Yield: 62%; Acidimetric titre: 97.9%.

Analysis for $C_{15}H_{25}NO_3 \cdot HCl$:

|  | C | H | N |
|---|---|---|---|
| Calculated % | 59.27 | 8.63 | 4.61 |
| Found % | 58.72 | 8.90 | 4.53 |

Endo-8-methyl-8-syn-ethyl-8-azoniabicyclo[3.2.1]octane-6,7-exo-epoxy-3-(2-propyl)pentanoate bromide.

1.1 g of endo-8-azabicyclo[3.2.1]-octane-6,7-exo-epoxy-3-(2-propyl)pentanoate (0.004 moles) are dissolved in 15 ml of acetonitrile, 0.9 ml of ethyl bromide are added, and the mixture heated under reflux for 8 hours.

After cooling, it is diluted with ethyl ether, made basic with ammonia and the solvent evaporated, the crude product then being purified by chromatography over silica (eluent acetone).

The product obtained is dissolved in 11 ml of anhydrous methylene chloride, 2.5 g of methyl bromide are added and the mixture allowed to react for 10 days at ambient temperature. After proceeding as described in Example 1, the required product is obtained.

1.15 g of endo-8-methyl-8-syn-ethyl-8-azoniabicyclo[3.2.1]octane-6,7-exo-epoxy-3-(2-propyl)pentanoate bromide are obtained.

Yield: 74%; Melting point: 190°–192° C.

Analysis for $C_{18}H_{32}BrNO_3$:

|  | C | H | N |
|---|---|---|---|
| Calculated % | 55.38 | 8.26 | 3.59 |
| Found % | 54.02 | 8.15 | 3.65 |

EXAMPLE 4

Process for preparing endo-8-methyl-8-syn-butyl-8-azoniabicyclo[3.2.1]octane-6,7-exo-epoxy-3-(2-propyl)pentanoate bromide (Compound No. 10 of Table 1—Method B).

5 grams of endo-8-azabicyclo[3.2.1]octane-6,7-exo-epoxy-3-(2-propyl)pentanoate (0.019 moles), prepared by the procedure described in Example 3, are reacted with 6 ml of butyl bromide in 25 ml of acetonitrile in the presence of 2.6 g of anhydrous $K_2CO_3$ under reflux for 6 days.

After cooling and filtering off the insoluble substance, the procedure described in Example 3 is followed to obtain the required product.

6.1 g of endo-8-methyl-8-syn-butyl-8-azoniabicyclo[3.2.1]octane-6,7-exo-epoxy-3-(2-propyl)pentanoate bromide are obtained.

Yield: 77%; Melting point: 176°–178° C.

Analysis for $C_{20}H_{36}BrNO_3$:

|  | C | H | N |
|---|---|---|---|
| Calculated % | 57.41 | 8.67 | 3.35 |
| Found % | 55.89 | 8.67 | 3.31 |

EXAMPLE 5

Process for preparing endo-8-methyl-8-syn-(1-methyl)ethyl-8-azoniabicyclo[3.2.1]octane-6,7-exo-epoxy-3-(2-propyl)pentanoate bromide (Compound No. 8 of Table 1—Method B).

4 grams of endo-8-azabicyclo[3.2.1]octane-6,7-exo-epoxy-3-(2-propyl)pentanoate (0.015 moles), prepared by the procedure described in Example 3, are reacted with 15 ml of isopropyl bromide in a Parr bomb at 80° C. under an inert atmosphere for 5 days.

The subsequent processing is in accordance with the procedure described in Example 4, to give the required product.

0.66 g of endo-8-methyl-8-syn-(1-methyl)ethyl-8-azoniabicyclo[3.2.1]octane-6,7-exo-epoxy-3-(2-propyl)-pentanoate bromide are obtained.

Yield: 11%; Melting point: 214°–216° C.

Analysis for $C_{19}H_{34}BrNO_3$:

|  | C | H | N |
|---|---|---|---|
| Calculated % | 56.43 | 8.47 | 3.46 |
| Found % | 56.23 | 8.53 | 3.53 |

Other endo-8,8-dialkyl-8-azoniabicyclo[3.2.1]octane-6,7-exo-epoxy-3-alkylcarboxylate salts were synthesized by the processes described in the preceding examples.

Table 1 comprises the main compounds of general formula (I) prepared by the described methods.

$R_1$, $R_2$, $R_3$, $R_4$, X represent the symbols appearing in formula (I).

TABLE 1

| Compound No. | $R_1$ | $R_2$ | $R_3$ | $R_4$ | X | Prep. method | R % | C | H | N |
|---|---|---|---|---|---|---|---|---|---|---|
| 1 | $CH_3$ | $CH_3$ | $CH_3$ | $CH_3$ | Br | A | 63 | 48.74 | 6.93 | 4.37 |
|   |   |   |   |   |   |   |   | 47.81 | 6.65 | 4.32 |
| 2 | $CH_3$ | $CH_3$ | n-$C_3H_7$ | n-$C_3H_7$ | Br | A | 56 | 54.25 | 8.03 | 3.72 |
|   |   |   |   |   |   |   |   | 52.61 | 8.06 | 3.40 |
| 3 | $CH_3$ | $CH_3$ | n-$C_3H_7$ | n-$C_3H_7$ | I | A | 51 | 48.21 | 7.15 | 3.31 |
|   |   |   |   |   |   |   |   | 48.50 | 7.22 | 3.30 |
| 4 | $CH_3$ | $C_2H_5$ | $C_2H_5$ | $C_2H_5$ | Br | B | 64 | 53.02 | 7.79 | 3.87 |
|   |   |   |   |   |   |   |   | 53.85 | 7.84 | 3.91 |

TABLE 1-continued

| Compound No. | $R_1$ | $R_2$ | $R_3$ | $R_4$ | X | Prep. method | R % | C | H | N |
|---|---|---|---|---|---|---|---|---|---|---|
| 5 | $CH_3$ | $C_2H_5$ | n-$C_3H_7$ | n-$C_3H_7$ | Br | B | 74 | 55.38 | 8.26 | 3.59 |
|   |   |   |   |   |   |   |   | 54.02 | 8.15 | 3.65 |
| 6 | $CH_3$ | n-$C_3H_7$ | n-$C_3H_7$ | n-$C_3H_7$ | Br | B | 48 | 56.43 | 8.47 | 3.46 |
|   |   |   |   |   |   |   |   | 56.35 | 8.39 | 3.50 |
| 7 | $CH_3$ | n-$C_3H_7$ | n-$C_3H_7$ | n-$C_3H_7$ | I | B | 45 | 54.19 | 7.03 | 2.87 |
|   |   |   |   |   |   |   |   | 54.11 | 7.21 | 2.81 |
| 8 | $CH_3$ | i-$C_3H_7$ | n-$C_3H_7$ | n-$C_3H_7$ | Br | B | 11 | 56.43 | 8.47 | 3.46 |
|   |   |   |   |   |   |   |   | 56.23 | 8.53 | 3.53 |
| 9 | $CH_3$ | n-$C_4H_9$ | $C_2H_5$ | $C_2H_5$ | I | B | 12 | 49.41 | 7.38 | 3.20 |
|   |   |   |   |   |   |   |   | 49.35 | 7.26 | 3.17 |
| 10 | $CH_3$ | n-$C_4H_9$ | n-$C_3H_7$ | n-$C_3H_7$ | Br | B | 77 | 57.41 | 8.67 | 3.35 |
|   |   |   |   |   |   |   |   | 55.89 | 8.67 | 3.31 |
| 11 | $C_2H_5$ | $CH_3$ | $C_2H_5$ | $C_2H_5$ | Br | A | 67 | 53.02 | 7.79 | 3.87 |
|   |   |   |   |   |   |   |   | 53.00 | 7.68 | 3.85 |
| 12 | $C_2H_5$ | $CH_3$ | n-$C_3H_7$ | n-$C_3H_7$ | Br | A | 85 | 55.38 | 8.26 | 3.59 |
|   |   |   |   |   |   |   |   | 53.93 | 8.29 | 3.40 |
| 13 | $C_2H_5$ | $CH_3$ | n-$C_3H_7$ | n-$C_3H_7$ | I | A | 68 | 49.41 | 7.38 | 3.20 |
|   |   |   |   |   |   |   |   | 49.48 | 7.46 | 3.23 |
| 14 | $C_2H_5$ | $C_2H_5$ | $CH_3$ | $CH_3$ | Br | B | 54 | 51.71 | 7.53 | 4.02 |
|   |   |   |   |   |   |   |   | 50.98 | 7.66 | 4.00 |
| 15 | $C_2H_5$ | $C_2H_5$ | $C_2H_5$ | $C_2H_5$ | Br | B | 51 | 54.23 | 8.04 | 3.72 |
|   |   |   |   |   |   |   |   | 54.02 | 8.15 | 3.67 |
| 16 | $C_2H_5$ | $C_2H_5$ | n-$C_3H_7$ | n-$C_3H_7$ | Br | B | 60 | 56.41 | 8.48 | 3.46 |
|   |   |   |   |   |   |   |   | 56.39 | 8.53 | 3.39 |
| 17 | $C_2H_5$ | $C_2H_5$ | n-$C_3H_7$ | n-$C_3H_7$ | I | B | 58 | 50.53 | 7.60 | 3.10 |
|   |   |   |   |   |   |   |   | 50.00 | 6.89 | 3.02 |
| 18 | $C_2H_5$ | n-$C_3H_7$ | n-$C_3H_7$ | n-$C_3H_7$ | Br | A | 48 | 57.39 | 8.68 | 3.35 |
|   |   |   |   |   |   |   |   | 56.99 | 8.75 | 3.28 |
| 19 | $C_2H_5$ | n-$C_3H_7$ | n-$C_3H_7$ | n-$C_3H_7$ | I | A | 43 | 51.59 | 7.80 | 3.01 |
|   |   |   |   |   |   |   |   | 50.98 | 7.65 | 3.03 |
| 20 | $C_2H_5$ | n-$C_4H_9$ | n-$C_3H_7$ | n-$C_3H_7$ | I | A | 40 | 52.59 | 7.99 | 2.92 |
|   |   |   |   |   |   |   |   | 51.80 | 7.97 | 2.84 |
| 21 | n-$C_3H_7$ | $CH_3$ | n-$C_3H_7$ | n-$C_3H_7$ | Br | A | 44 | 56.41 | 8.48 | 3.46 |
|   |   |   |   |   |   |   |   | 56.28 | 8.41 | 3.40 |
| 22 | n-$C_3H_7$ | $CH_3$ | n-$C_3H_7$ | n-$C_3H_7$ | I | A | 42 | 50.53 | 7.60 | 3.10 |
|   |   |   |   |   |   |   |   | 51.00 | 7.67 | 3.12 |

As a result of pharmacological screening, the compounds according to the invention shown in Table 1 were found to possess interesting spasmolytic activity without those side effects which are characteristic of antispastic drugs in general.

The study was conducted using the following in vitro and in vivo tests, each time in comparison with Buscopan, atropine methyl bromide and syntropium bromide:
1. Isolated rat ileum (antagonist barium chloride)
2. Isolated guinea pig ileum (antagonist acetyl choline)
3. Intestinal transit in the mouse
4. Mydriatic activity in the mouse
5. Acute toxicity in the mouse

A—IN VITRO TEST

1. Isolated rat ileum

The spasmolytic activity of the compounds reported in Table 1 were studied firstly in a comparison with Buscopan (scopolamine butyl bromide), using the isolated rat ileum, by the classical Magnus method [Magnus and coll., Pflugers Gas. Physiol., 102, 123 (1904)], of which the smooth muscle was subjected to direct stimulation by barium chloride. The evaluation of this activity was made by the method involving the $pA_2$ determination [Schild H. G., Brit. J. Pharmacol., 2, 189, (1947)]. The $pA_2$ value is the negative logarithm of the molar concentration of the antagonist able to reduce the contraction induced by the antagonist (barium chloride) by 50%.

Table 2 shows by way of example the $pA_2$ values of some of the compounds of the described class, these compounds being identified by the number given in Table 1. The table also shows the activity ratios with respect to Buscopan, calculated as the antilogarithms of the difference between the respective values of $pA_2$.

As can be seen, compounds Nos. 2 and 5 are the most active in this test, and have a direct myolytic activity which is respectively 16.6 and 7.8 times that of Buscopan (activity=1), and compound No. 12 appears to have an activity similar to that of Buscopan (activity only 1.5 times lower). Compound No. 8, although not being on the same level as buscopan, still has good spasmolytic activity.

TABLE 2

Spasmolytic effect evaluated on the isolated rat ileum with barium chloride as antagonist, and expressed as the $pA_2$ value.

| Compound | Number of experiments | $pA_2$ | Confidence limits (P = 0.05) | Activity ratio |
|---|---|---|---|---|
| Buscopan | 6 | 6.84 | 6.75–6.95 | 1 |
| No. 2 | 6 | 8.06 | 7.85–8.84 | 16.6 |
| No. 5 | 6 | 7.73 | 7.50–8.24 | 7.8 |
| No. 8 | 6 | 5.72 | 5.49–6.23 | 0.08 |
| No. 12 | 6 | 6.66 | 6.42–7.02 | 0.7 |

2. Isolated guinea pig ileum

All the compounds were also tested for antimuscarinic activity using the isolated guinea pig ileum, with acetyl choline as antagonist.

The potency of action was evaluated by calculating the $pA_2$ values, as in the case of the direct myolytic activity evaluated on the isolated rat ileum.

Table 3 shows the $pA_2$ values for the compounds already given in the preceding table, compared both with Buscopan and with syntropium bromide.

Again in this pharmacological test, compounds Nos. 2 and 5 showed an interestingly strong spasmolytic activity of 4.27 and 2.45 times that of Buscopan.

In fact, all products have strong spasmolytic activity.

Furthermore, both compound No. 2 and compound No. 5 show an antimuscarinic activity which approaches that of atropine itself, and is in the first case much higher than and in the second case similar to that of syntropium bromide.

TABLE 3

Antimuscarinic activity evaluated on the isolated guinea pig ileum with acetyl choline as antagonist, expressed as $pA_2$ value.

| Compound | Number of experiments | $pA_2$ | Confidence limits (P = 0.05) | Activity ratio |
|---|---|---|---|---|
| Buscopan | 6 | 7.33 | 7.25–7.43 | 1 |
| Syntropium Br | 6 | 7.74 | 7.49–8.41 | 2.57 |
| No. 2 | 6 | 7.96 | 7.75–8.38 | 4.27 |
| No. 5 | 6 | 7.72 | 7.49–8.23 | 2.25 |
| No. 8 | 6 | 6.52 | 6.38–6.73 | 0.15 |
| No. 12 | 6 | 7.03 | 6.91–7.21 | 0.50 |

B—IN VIVO TEST
3. intestinal transit in the mouse

An evaluation was made on the capacity of the studied compounds to inhibit the progression of an opaque meal 15 minutes after their intraperitoneal administration into the mouse. This test is indicative of undesirable side effects.

The method followed was the classical method of Janssen and Jageneau [Janssen P. A., Jageneau A. H., J. Pharm. Pharmacol. 9, 381 (1957)], by which the doses which inhibit the progression of the opaque meal through the small intestine by 50% ($ED_{50}$) relative to the controls were calculated.

Table 4 shows the values obtained for some of the compounds according to the invention, compared with Buscopan, atropine methyl bromide and syntropium bromide.

As can be seen, although compounds Nos. 2 and 5 have both a direct and antimuscarinic spasmolytic activity which is better than the corresponding activities of Buscopan, they reduce intestinal transit to a decidedly lesser extent.

TABLE 4

Activity affecting intestinal transit in the mouse after intraperitonal administration 15 minutes before taking the opaque meal.

| Compound | $ED_{50}$ mg/kg/i.p. | Confidence limits (P = 0.05) mg/kg/i.p. |
|---|---|---|
| Buscopan | 51.69 | 35.83–74.57 |
| Atropine MeBr | 52.06 | 32.77–82.69 |
| Syntropium Br | 29.82 | 25.46–34.93 |
| No. 2 | 78.96 | 65.13–95.72 |
| No. 5 | 73.17 | 44.08–121.44 |
| No. 8 | approx. 69 | — |
| No. 10 | approx. 85 | — |
| No. 12 | 42.19 | 39.82–44.70 |

4. Mydriatic activity in the mouse

Compounds Nos. 2 and 5, which were found to be the most interesting as spasmolytics, were also evaluated in terms of their mydriatic action, which is indicative of undesirable side effects.

The dose able to increase the basal pupillary diameter by 150% ($ED_{150}$) 15 minutes, 30 minutes, 60 minutes and 120 minutes after intraperitoneal administration of the compounds into the mouse was calculated.

Compared with atropine methyl bromide, which is considered the reference standard in this type of test, the compounds show considerably lower activity, which for compound No. 2 is of one order of magnitude (10 times less), and for compound No. 5 is of more than two orders of magnitude (>100 times less).

It is also interesting to observe that this mydriatic activity rapidly falls off with time, in contrast to atropine methyl bromide, and more especially to Buscopan which still possesses activity 120 minutes after its administration.

TABLE 2

Mydriatic activity evaluated in the mouse 15 minutes, 30 minutes, 60 minutes and 120 minutes after intraperitoneal administration

| Compound | Dose range (mg/kg) | $ED_{150}$ (mg/kg/i.p.) | | | |
|---|---|---|---|---|---|
| | | after 15 min | after 30 min | after 60 min | after 120 min |
| Atropine MeBr | 0.012–0.1 | 0.030 (0.026–0.035) | 0.030 (0.027–0.034) | 0.052 (0.042–0.066) | not determinable |
| Buscopan | 2–8 | 3.24 (2.68–3.92) | 3.29 (2.86–3.79) | 3.66 (3.35–3.99) | 5.32 (4.75–5.76) |
| No. 2 | 0.125–4 | 0.21 (0.16–0.28) | 0.42 (0.34–0.50) | 1.46 (1.16–1.84) | not determinable |
| No. 5 | 1–8 | 2.17 (1.81–2.59) | 6.16 (4.61–8.23) | not determinable | not determinable |

5. Acute toxicity in the mouse

The acute toxicity of the compounds according to the invention was evaluated in comparison with that of Buscopan, atropine methyl bromide and syntropium bromide, after intraperitoneal administration in male mice (Swiss stock).

The $LD_{50}$, the values of which together with the relative confidence limits (P=0.05) are given in Table 6, was calculated by the Litchfield and Wilcoxon method [Litchfield J. T., Wilcoxon F. A., J. Pharmac. Exp. Theor., 96, 99 (1949)].

As can be seen, the values for the studied compounds are analogous to those of the reference standards, with the exception of compounds Nos. 2 and 10, which have a decidedly lower toxicity.

TABLE 6

Acute toxicity in the mouse after intraperitoneal administration

| Compound | $LD_{50}$ mg/kg/i.p. | Confidence limits (P = 0.05) mg/kg/i.p. |
|---|---|---|
| Buscopan | 65 | 57.0–70.2 |
| Atropine MeBr | 75 | 65.8–85.5 |
| Syntropium Br | 65 | 40.5–62.3 |
| No. 2 | 93.5 | 76.0–115.0 |
| No. 5 | 74 | 66.7–82.1 |
| No. 8 | 78 | 73.6–82.7 |
| No. 10 | 105 | 78.3 140.7 |
| No. 12 | 72 | 67.9–76.3 |

In conclusion, from the pharmacological analysis of the new products according to the invention it thus appears apparent that they are all spasmolytic products practically free from side effects. In particular, the compounds indicated by the numbers 2 and 5 have both a direct and antimuscarinic spasmolytic activity which is decidedly greater than those of Buscopan (see Tables 2 and 3). This greater potency of action is accompanied by a lesser level of side effects and a lower toxicity, as can be observed from the data obtained regarding intestinal transit and the mydriatic effect in the mouse given in Tables 4, 5 and 6.

As is well known, research in the spasmolytics field is always directed towards identifying compounds which have a clean spasmolytic effect, ie free from those side effects which generally compromise and limit their application.

We claim:

1. Endo-8,8-dialkyl-8-azoniabicyclo[3.2.1]octane-6,7-exo-epoxy-3-alkylcarboxylate compounds of formula

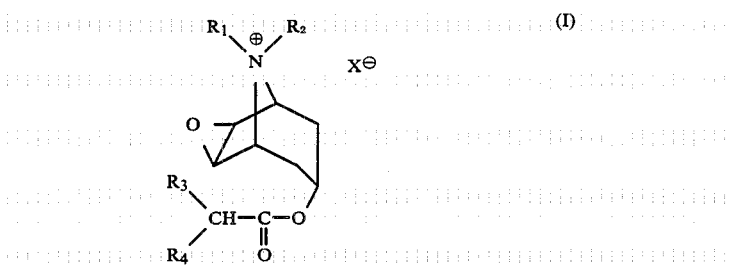

in which
  $R_1$ and $R_2$, which can be the same or different, are linear or branched alkyl radicals of 1–5 carbon atoms or cycloalkyl radicals of 3–6 carbon atoms;
  $R_3$ and $R_4$, which can be the same or different, are linear or branched alkyl radicals of 1–6 carbon atoms;
  X is Br, Cl or I.

2. The compound endo-8,8-dimethyl-8-azoniabicyclo[3.2.1]octane-6,7-exo-epoxy-3-(2-propyl)pentanoate bromide.

3. The compound endo-8-methyl-8-syn-ethyl-8-azoniabicyclo[3.4.1]octane-6,7-exo-epoxy-3-(2-propyl)-pentanoate bromide.

4. A therapeutic composition comprising: a spasmolytically effective amount of the compound of formula (I), as defined in claim 1, and a pharmaceutically acceptable carrier.

* * * * *